United States Patent [19]

Tsuchida et al.

[11] 4,427,773

[45] Jan. 24, 1984

[54] METHOD FOR PRODUCING L-GLUTAMIC ACID BY FERMENTATION

[75] Inventors: Takayasu Tsuchida, Kawasaki; Kiyoshi Miwa, Matsudo; Shigeru Nakamori, Yokohama; Haruo Momose, Kamakura, all of Japan

[73] Assignee: Ajinomoto Company Incorporated, Tokyo, Japan

[21] Appl. No.: 255,169

[22] Filed: Apr. 17, 1981

[30] Foreign Application Priority Data

Apr. 17, 1980 [JP] Japan .................................. 55-51001
Apr. 17, 1980 [JP] Japan .................................. 55-51002

[51] Int. Cl.$^3$ ...................... C12N 15/00; C12N 1/00; C12P 13/14
[52] U.S. Cl. .................................. 435/110; 435/172; 435/243; 435/840; 435/843
[58] Field of Search ............... 435/110, 172, 317, 243, 435/840, 843

[56] References Cited

U.S. PATENT DOCUMENTS

4,278,765  7/1981  Debabov et al. .................... 435/115

FOREIGN PATENT DOCUMENTS

52-2038088  3/1977  Japan .................................. 435/172

OTHER PUBLICATIONS

Chakrabarty, *Genetic Engineering*, C.R.C. Press, Inc., Palm Beach, 1978, pp. 101 and 105.

*Primary Examiner*—Albert T. Meyers
*Assistant Examiner*—Kathleen S. McCowin
*Attorney, Agent, or Firm*—Oblon, Fisher, Spivak, McClelland & Maier

[57] ABSTRACT

An L-glutamic acid producing microorganism which is constructed by incorporation into a recipient strain of the genus Brevibacterium or Corynebacterium of a hybrid plasmid having inserted therein a DNA fragment with genetic information related to L-glutamic acid production which is derived from a donor strain of the genus Brevibacterium or Corynebacterium, is useful for the production of high levels of L-glutamic acid by fermentation.

9 Claims, No Drawings

METHOD FOR PRODUCING L-GLUTAMIC ACID BY FERMENTATION

BACKGROUND OF THE INVENTION

1. Field of the Invention

The present invention relates to a method for producing L-glutamic acid by fermentation.

2. Description of the Prior Art

Various L-glutamic acid producing bacterial wild strains are known especially in the genus Brevibacterium or Corynebacterium. In order to increase L-glutamic acid productivity of the known wild strains, artificial mutation is given to the wild strains.

Examples of such artificial mutants are mutants of Brevibacterium resistant to S-2-amino-ethyl-cysteine (Japanese Published Unexamined Patent Application No. 126877/1975), mutants of Brevibacterium and Corynebacterium resistant to fluorocitric acid, ketomalonic acid, α-amino-β-hydroxyvaleric acid, DL-threoninehydroxamate, 2-amino-3-phosphopropionic acid or 5-aminolevulinic acid (Japanese Published Unexamined Patent Application No. 89045/1979), mutants of Brevibacterium and Corynebacterium sensitive to lysozyme (Japanese Published Unexamined Patent Application No. 122794/1979), mutants of Brevibacterium and Corynebacterium having reduced activity of pyruvic acid dehydrogenase (Japanese Published Unexamined Patent Application No. 21762/1980), mutants resistant to glutamic acid or glutamic acid-analgue of Brevibacterium or Corynebacterium (Japanese Published Unexamined Patent Application No. 21763/1980), and mutants of Brevibacterium resistant to 2,6-pyridine-dicarboxylic acid (Japanese Published Unexamined Patent Application No. 21764/1980).

It has, however, become difficult to increase the yields of L-glutamic acid by the artificial mutation techniques. A need therefore, continues to exist for the development of novel microorganisms capable of producing L-glutamic acid in high yields.

SUMMARY OF THE INVENTION

It is therefore an object of the present invention to provide a method for producing L-glutamic acid in high yield.

This and other objects of the invention, which will hereinafter become more readily apparent, have been attained by providing a method for producing L-glutamic acid which comprises:

(a) culturing in a culture medium an L-glutamic acid producing microorganism which is constructed by incorporating into a recipient strain of the genus Brevibacterium or Corynebacterium, a hybrid plasmid having inserted therein a DNA fragment which is obtained from an L-glutamic acid producing bacterium of the genus Brevibacterium and Corynebacterium, and (b) recovering the L-glutamic acid accumulated in the culture medium.

DETAILED DESCRIPTION OF THE PREFERRED EMBODIMENTS

The DNA donor used to construct the L-glutamic acid producer of this invention is an L-glutamic acid producing bacterium of the genus Brevibacterium or Corynebacterium. Examples of wild strains of such L-glutamic acid producing bacteria are:

*Brevibacterium divaricatum:* ATCC 14020
*Brevibacterium flavum:* ATCC 13826
*Brevibacterium immariophilum:* ATCC 14068
*Brevibacterium lactofermentum:* ATCC 13869
*Brevibacterium roseum:* ATCC 13825
*Brevibacterium saccharolyticum:* ATCC 14066
*Brevibacterium thiogenitalis:* ATCC 19240
*Corynebacterium acetoacidophilum:* ATCC 13870
*Corynebacterium acetoglutamicum:* ATCC 15806
*Corynebacterium callunae:* ATCC 15991
*Corynebacterium lilium:* ATCC 15990
*Corynebacterium melassecola:* ATCC 17965
*Corynebacterium glutamicum:* ATCC 13032

Artificial mutants derived from the wild strains mentioned above can be of course used as the DNA donor if the mutants have the productivity of L-glutamic acid. Better result will be obtained when bacterium having higher productivity of L-glutamic acid is used as the DNA donor.

The recipients are wild or mutant strains of the genus Brevibacterium or Corynebacterium. Especially, it is convenient to use L-glutamic acid requiring mutant to select hybrid clones transformed to produce L-glutamic acid. Wild or mutant strains having higher productivity of L-glutamic acid is desirable as the recipient. In the case where L-glutamic acid requiring mutant is used as the recipient, desirably the mutant is induced from a parent strain having higher productivity of L-glutamic acid.

In order to increase the L-glutamic acid-productivity of the recipient or the parent strain of the L-glutamic acid requiring mutant, requirement for a nutrient, such as L-lysine, L-threonine, L-isoleucine, L-proline, L-arginine, L-methionine, L-histidine, L-leucine, L-tryptophan, L-tyrosine, L-phenylalanine, L-alanine, L-serine, glycine, Xanthine, hypoxanthine, adenine or guanine, is given to the L-glutamic acid producing bacterium by mutation. L-Glutamic acid productivity is also increased by giving to the L-glutamic acid producing bacterium sensitivity to high temperature or to polyoxysorbitane-mono-palmitate, or resistance to monofluoro-acetic acid, ketomalonic acid, guanidine, sulfaguanidine, 2-thiazolealanine or fluorophenylalanine, as is known.

Chromosomal DNA is extracted from the DNA donor in a well-known manner and treated with a restriction endonuclease by a well-known method (Biochem. Biophys. Acta 383: 457 (1975)). Although various kinds of restriction endonuclease are applicable if the digestion is made partly. According to the inventors findings, Hind III, Bcl I, Xba I and Xma I are most preferred for the digestion purpose.

As the vector DNA, plasmid or phage DNA extracted from the L-glutamic acid producing bacteria of the genus Brevibacterium or Corynebacterium, or derivative of the plasmid or phage is used. The vector DNA is digested also with restriction endonuclease. Preferred restriction endonuclease are Hind III, Bcl I, Xba I and Xma I.

The digested chromosomal and vector DNAs are subjected to a ligation reaction with ligase.

Recombination of DNA to prepare the recombinant plasmid can be carried out by incorporating with terminal transferase deoxyadenylic acid and thymidylic acid, or deoxyguanylic acid and deoxycytidylic acid into the chromosomal DNA fragment and cleaved vector DNA, and by subjecting the modified chromosomal DNA fragment and cleaved DNA to an annealing reaction.

The hybrid DNA thus obtained can be incorporated into the recipient microorganism by conventional transformation techniques, and the recipients are thereafter allowed to grow for a while to make the transformed characteristics of transformant stable. Desired transformant can be selected by screening clone having both or one of the characteristics of L-glutamic acid productivity and the characteristics possessed by the vector.

The L-glutamic acid producing bacteria thus obtained can be cultured by conventional manner to let it produce L-glutamic acid, such as at a pH of 6 to 8, and a temperature of 30° to 37° C. The cultivation is continued until the production of L-glutamic acid substantially ceases.

The culture medium employed is conventional and contains carbon source, nitrogen source, inorganic ions and when required minor organic nutrient. As the carbon source, glucose, sucrose and crude materials containing these carbohydrates (such as starch hydrolysate and molasses), organic acid such as acetic acid, and alcohol such as ethanol. Gaseous ammonia, aqueous ammonia, ammonium salts and urea can be used as the nitrogen source.

In the method of this invention, higher yield of L-glutamic acid can be obtained than known methods, and additionally recovering of L-glutamic acid can be carried out conveniently because by-products of amino acid in the culture liquid are scarce.

Having generally described this invention, a further understanding can be obtained by reference to certain specific examples which are provided herein for purposes of illustration only and are not intended to be limiting unless otherwise specified.

EXAMPLE 1

(1) Preparation of chromosomal DNA possessing genetic information related to L-glutamic acid

*Brevibacterium lactofermentum* No. 5116 (NRRL B-12405), a mutant sensitive to a high temperature and induced from strain No. 2256 (ATCC 13869), was cultured at 30° C. for 3 hours with shaking in 1 l of CMG-medium containing 1 g/dl peptone 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 3.5 mg of purified DNA was obtained.

(2) Preparation of vector DNA

As the vector, the DNA of plasmid pAM330 (M.W. $3 \times 10^6$ dalton) was prepared as follows:

A strain of *Brevibacterium lactofermentum* No. 2256 harboring the plasmid pAM 330 was incubated at 30° C. in 1 l of CMG-medium. After the strain was incubated until the late log phase, the cells were harvested and then lysed by treatment with lysozyme and SDS. The lysate was centrifuged at 30,000 Xg for 30 minutes to obtain a supernatant. After concentrating the supernatant, 74 μg of the plasmid DNA was obtained by fractionation using agarose gel electrophoresis.

(3) Insertion of chromosomal DNA fragment into vector

Ten μg of the chromosomal DNA was treated with each of the restriction endonucleases Hind III or Bcl 1 at 37° C. for 10, 30 and 60 minutes respectively, to cleave DNA chains, and then was heated at 65° C. for 5 minutes, respectively. Ten μg of the vector DNA was also treated with each of the restriction endonucleases, Hind III or Bcl I at 37° C. for 1 hour to cleave the DNA completely, and then was heated at 65° C. for 5 minutes, respectively.

The digested chromosomal DNA solution and the cleaved vector DNA solution were mixed and subjected to the ligation reaction of DNA fragments by a $T_4$ phage DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

(4) Genetic transformation with the hybrid plasmid harboring the genetic information related to glutamic acid production Glutamic acid requiring strains of *Brevibacterium lactofermentum* No. 3 (NRRL B-12406) or No. 4 (NRRL B-12407) which were derived from *Brevibacterium lactofermentum* No. 5116 by N-methyl-N'-nitro-N-nitrosoguanidine mutagenesis, were cultured in 20 ml of CMG at 30° C. with shaking. Cells in the exponential growth phase were harvested, and suspended in a 0.1 M $MgCl_2$ solution and then in a 0.1 M $CaCl_2$ solution in an ice-bath, whereby, "competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes. The cells, thus containing the hybrid plasmid DNA, were inoculated into an L-medium and the medium was shaken at 37° C. for 3 hours, whereby the transformation reaction was completed. The cells were harvested, washed, and resuspended. A small portion of the cell suspension was spread on an agar plate containing, 20 g glucose, 10 g $(NH_4)_2SO_4$, 2.5 g urea, 1 g $KH_2PO_4$, 0.4 g $MgSO_4.7H_2O$, 50 μg biotin, 200 μg thiamine hydrochloride, 0.01 g $FeSO_4.7H_2O$, 0.01 g $MnSO_4.4H_2O$ and 20 agar, per liter, (pH was adjusted to 7.2). The plate was incubated at 37° C. After 4 days incubation, all of the colonies which appeared were picked up, purified and isolated.

Strains which became capable of producing L-glutamic acid by the transformation were picked up as the transformants. Among the transformants, most high L-glutamic acid producer AJ 11561 (FERM-P 5469) (NRRL B-12408) and AJ 11562 (FERM-P 5470) (NRRL B-12409) were selected. AJ 11561 was obtained from recipient No. 3 using Hind III, and AJ 11562 was obtained from recipient No. 4 using Bcl I.

(5) Production of L-glutamic acid by the prepared glutamic acid producing strain L-Glutamic acid production of AJ 11561 and AJ 11562 was tested comparing with the DNA-donor and the recipients, as follows:

The fermentation medium contained 3.6 g/dl glucose, 0.5 g/dl urea, 0.1 g $KH_2PO_4$, 0.1 g/dl $MgSO_4.7H_2O$, 3 ml/dl soybean hydrolysate ("Mieki"), 100 μg/l thiamine.HCl 3 μg/l biotin, 1 mg/dl $FeSO_4.7H_2O$, 1 mg/dl $MnSO_4.4H_2O$ and 2.5 g/dl $CaCO_3$ (separately sterilized) and the pH was adjusted to 7.0.

Twenty ml of the fermentation medium was placed in 500 ml flasks, inoculated with one loopful inoculum of the test microorganisms, and the cultivation was performed at 31° C. for 48 hours.

The amounts of L-glutamic acid in the supernatant of the fermentation broth were determined by enzymatic assay.

TABLE 1

| Microorganisms tested | Amounts of L-glutamic acid accumulated (mg/dl) |
|---|---|
| Brevibacterium lactofermentum No. 5116 | 550 |
| Brevibacterium lactofermentum No. 3 | 0 |
| Brevibacterium lactofermentum No. 4 | 0 |
| Brevibacterium lactofermentum AJ 11561 | 980 |
| Brevibacterium lactofermentum AJ 11562 | 900 |

EXAMPLE 2

(1) Preparation of chromosomal DNA possessing genetic information related to L-glutamic acid production

*Corynebacterium glutamicum* No. 5707 (NRRLB-12410), a mutant resistant to ketomalonic acid and induced from *Corynebacterium glutamicum* AJ 11560 (FERM-P 5485) (NRRL B-12415), was cultured at 30° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 4.0 mg of purified DNA was obtained.

*Corynebacterium glutamicum* AJ 11560 was newly isolated as a suitable strain for the purpose of this invention.

This strain, AJ 11560, was classified to the section III of genus Corynebacterium described in Bergey's Manual of Determinative Bacteriology (8th edition, 1974). However, taxonomic characteristics of the species belonging to section III are not disclosed in the Manual, but only disclosed the names of species of section III. Therefore, all original reports disclosed in the Manual as to section III are referred to. AJ 11560 was identified with *Corynebacterium glutamicum* described in "Bull. Agr. Chem. Soc. Japan, 22, 176~185 (1958)" and "J. Gen. Appl. Microbiol., 13, 279~301 (1967)".

(2) Preparation of vector DNA

As the vector, the DNA of plasmid PAM286 (M.W. $3 \times 10^6$ dalton) was prepared as follows:

A strain of *Corynebacterium glutamicum* AJ 11560 harboring the plasmid pAM286 was incubated at 30° C. in 1 l of CMG-medium. After the strain was incubated until the late log phase, the cells were harvested and then lysed by treatment with lysozyme and SDS. The lysate was centrifuged at 30,000 Xg for 30 minutes to obtain a supernatant. After concentrating the supernatant, 60 μg of the plasmid DNA was obtained by fractionation using agarose gel electrophoresis.

(3) Insertion of chromosomal DNA fragment into vector Ten μg of the chromosomal DNA was treated with each of the restriction endonucleases Hind III or Xma I at 37° C. for 10, 30 and 60 minutes respectively, to cleave DNA chains, and then was heated at 65° C. for 5 minutes, respectively. Ten μg of the vector DNA was also treated with each of the restriction endonucleases, Hind III or Xma I at 37° C. for 1 hour to cleave the DNA completely, and then was heated at 65° C. for 5 minutes, respectively.

The digested chromosomal DNA solution and the cleaved vector DNA solution were mixed and subjected to the ligation reaction of DNA fragments by a $T_4$ phage DNA-ligase in the presence of ATP and dithiothreitol at 10° C. for 24 hours. The reacton mixture was then heated at 65° C. for 5 minutes, and two fold volumes of ethanol were added to it. The recombinant DNA which precipitated was recovered.

(4) Genetic transformation with the hybrid plasmid harboring the genetic information related to glutamic acid production L-Glutamic acid requiring strains of *Corynebacterium glutamicum* No. 12 (NRRL B-12411) and No. 26 (NRRL B-12412), which were derived from *Corynebacterium glutamicum* No. 5707 by N-methyl-N'-nitro-N-nitrosoguanidine mutagenesis, were cultured in 20 ml of CMG-medium at 30° C. with shaking. Cells in the exponential growth phase were harvested, and suspended in a 0.1 M $MgCl_2$ solution and then in a 0.1 M $CaCl_2$ solution in an ice-bath, whereby, "competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes. The cells, thus containing the hybrid plasmid DNA, were inoculated into an L-medium and the medium was shaken at 37° C. for 3 hours, whereby the transformation reaction was completed. The cells were harvested, washed, and resuspended. The reaction mixture, after having been diluted, of the cell suspension was spread on an agar plate containing, 20 g glucose, 10 g $(NH_4)_2SO_4$, 2.5 g urea, 1 g $KH_2PO_4$, 0.4 g $MgSO_4.7H_2O$, 50 μg biotin, 20 μg thiamine hydrochloride, 0.01 g $FeSO_4.7H_2O$, 0.01 g $MnSO_4.4H_2O$ and 20 g agar, per liter, (pH was adjusted to 7.0). The plate was incubated at 37° C. After 4 days incubation, all of the colonies which appeared were picked up, purified and isolated.

AJ 11566 (FERM-P 5486)(NRRL B-12413) from the recipient strain No. 12 using Hind III, and AJ 11567 (FERM-P 5487) (NRRL B-12414) was obtained from the recipient strain No. 26 using Xma I.

(5) Production of L-glutamic acid by the prepared glutamic acid producing strain The transformants obtained in step (4) were cultured to test their L-glutamic acid productivity. The DNA-donor strain No. 5707 and the recipients strains were cultured in the same manner for comparison.

The culture medium contained 3.6 g/dl glucose, 0.5 g/dl urea, 0.1 g $KH_2PO_4$, 0.1 g/dl $MgSO_4.7H_2O$, 3 ml/dl soybean hydrolysate ("Mieki"), 100 μg/l thiamine.HCl 3 μg/l biotin, 1 mg/dl $FeSO_4.7H_2O$, 1 mg/dl $MnSO_4.4H_2O$ and 2.5 g/dl $CaCO_3$ (separately sterilized) and the pH was adjusted to 7.0.

Twenty ml of the fermentation medium was placed in a 500 ml flasks, inoculated with one loopful inoculum of the test microorganisms, and the cultivation was performed at 31° C. for 48 hours.

The amounts of L-glutamic acid in the supernatant of the fermentation broth were determined by enzymatic assay.

TABLE 1

| Microorganisms tested | Amounts of L-glutamic acid accumulated (mg/dl) |
|---|---|
| Corynebacterium glutamicum No. 5707 | 600 |
| Corynebacterium glutamicum No. 12 | 0 |
| Corynebacterium glutamicum No. 26 | 0 |
| Corynebacterium glutamicum AJ 11566 | 1010 |
| Corynebacterium glutamicum AJ 11567 | 1000 |

What is claimed is:

1. The L-glutamic acid producing transformant which is *Brevibacterium lactofermentum* NRRL B-12408.

2. The L-glutamic acid producing transformant which is *Brevibacterium lactofermentum* NRRL B-12409.

3. The L-glutamic acid producing transformant which is *Corynebacterium glutamicum* NRRL B-12413.

4. The L-glutamic acid producing transformant which is *Corynebacterium glutamicum* NRRL B-12414.

5. A method for producing L-glutamic acid which comprises: (a) culturing in a culture medium an L-glutamic acid producing microorganism selected from the group consisting of *Brevibacterium lactofermentum* NRRL B-12409, *Brevibacterium lactofermentum* NRRL B-12408, *Corynebacterium glutamicum* NRRL B-12413, and *Corynebacterium glutamicum* NRRL B-12414 and (b) recovering the L-glutamic acid accumulated in the culture medium.

6. The method of claim 5, wherein said microorganism is *Brevibacterium lactofermentum* NRRL B-12408.

7. The method of claim 5, wherein said microorganism is *Brevibacterium lactofermentum* NRRL B-12409.

8. The method of claim 5, wherein said microorganism is *Corynebacterium glutamicum* NRRL B-12413.

9. The method of claim 5, wherein said microorganism is *Corynebacterium glutamicum* NRRL B-12414.

* * * * *